(12) United States Patent
Williams

(10) Patent No.: US 7,533,992 B2
(45) Date of Patent: May 19, 2009

(54) LIGHT SOURCE FOR DIAGNOSTIC INSTRUMENTS

(75) Inventor: William James Williams, Liverpool (GB)

(73) Assignee: WJW Ltd., Liverpool (GB)

( * ) Notice: Subject to any disclaimer, the term of this patent is extended or adjusted under 35 U.S.C. 154(b) by 508 days.

(21) Appl. No.: 10/482,122

(22) PCT Filed: May 24, 2002

(86) PCT No.: PCT/GB02/02454

§ 371 (c)(1),
(2), (4) Date: Jun. 28, 2004

(87) PCT Pub. No.: WO03/001990

PCT Pub. Date: Jan. 9, 2003

(65) Prior Publication Data

US 2004/0252278 A1    Dec. 16, 2004

(30) Foreign Application Priority Data

Jun. 29, 2001    (GB) ................................. 0115896.3

(51) Int. Cl.
*A61B 3/10* (2006.01)
*A61B 3/02* (2006.01)

(52) U.S. Cl. ................... 351/221; 351/216; 351/233; 351/243

(58) Field of Classification Search ................. 351/221, 351/204, 205, 211, 216, 218, 222, 233, 243, 351/243 T
See application file for complete search history.

(56) References Cited

U.S. PATENT DOCUMENTS

| | | | | |
|---|---|---|---|---|
| 4,849,755 A | * | 7/1989 | Benas | ........................ 340/946 |
| 5,202,708 A | | 4/1993 | Sasaki et al. | |
| 6,183,086 B1 | * | 2/2001 | Neubert | ...................... 351/221 |
| 6,643,546 B2 | * | 11/2003 | Mathis et al. | .................. 607/9 |

FOREIGN PATENT DOCUMENTS

| | | |
|---|---|---|
| EP | 0 910 986 | 4/1999 |
| EP | 1 127 534 | 8/2001 |
| WO | WO-00/71020 | 11/2000 |
| WO | WO-01/49166 | 7/2001 |

OTHER PUBLICATIONS

International Search Report for PCT/GB02/02454, date mailed on Jan. 10, 2003, 6 pages.

* cited by examiner

*Primary Examiner*—Scott J Sugarman
*Assistant Examiner*—Brandi N Thomas
(74) *Attorney, Agent, or Firm*—Morrison & Foerster LLP

(57) ABSTRACT

A new light source (e.g. LEDs) enables new designs in all or some key elements within diagnostic instruments. New light sources allow improvements in life of light source, infra red emitted, power consumption, color temperature, light flux directionality, simplification of optics design, adaptation of light flux directionality, and overall constructional simplification. The new light source allows for the replacement of some or all of the components designed for incandescent filament bulbs. The improved light source may allow for either an entirely new design of all or some core modules of the instrument, or by alteration of pre-existing modules.

32 Claims, 9 Drawing Sheets

Figure 11:
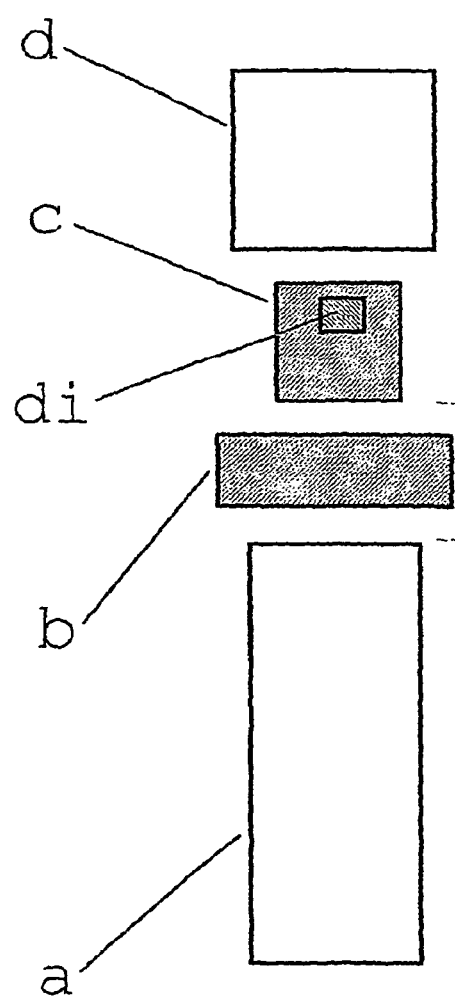

FIG 1
FIG 2
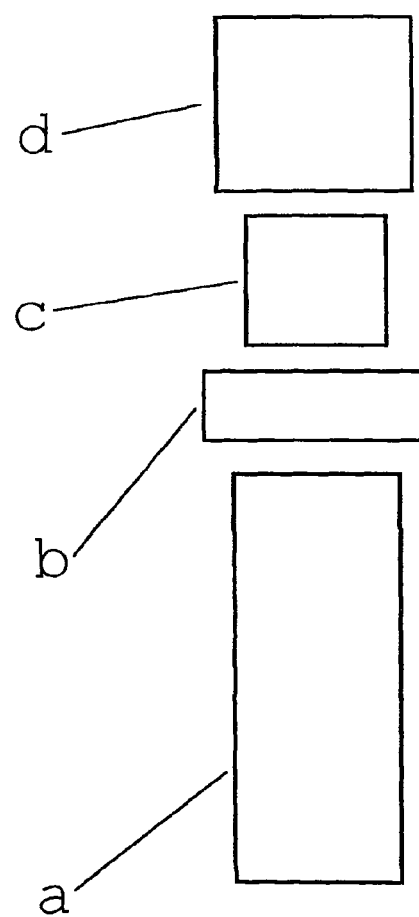
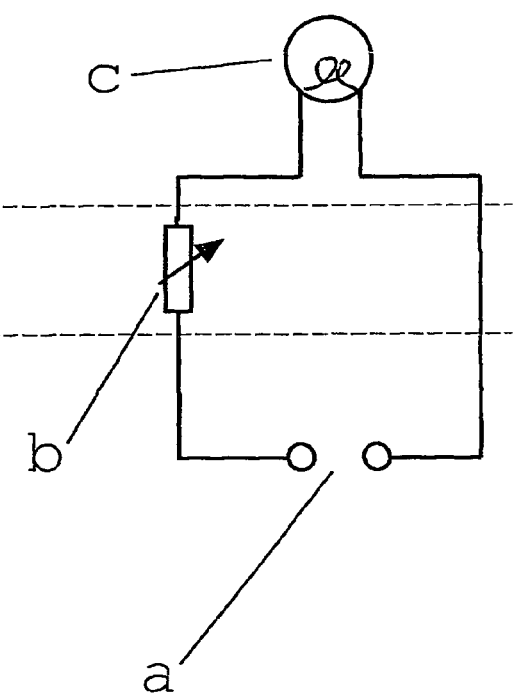

FIG 3
FIG 4
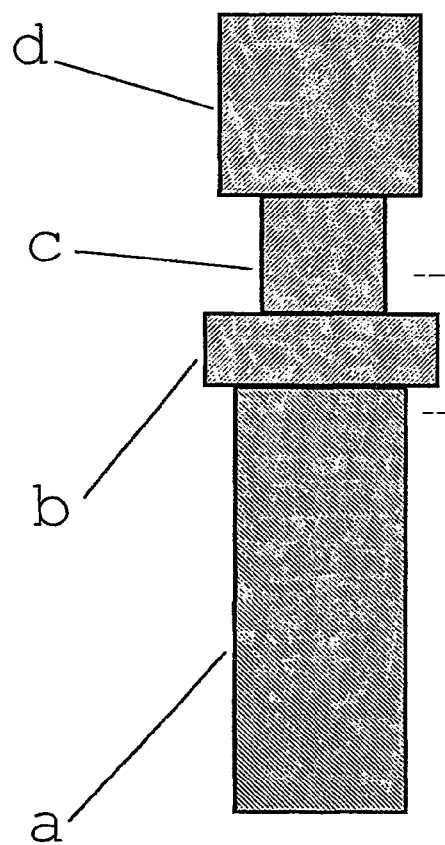
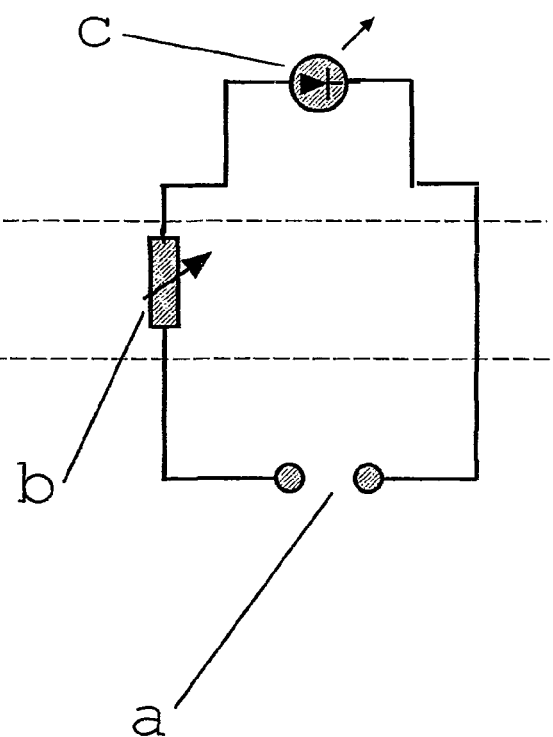

FIG 5
FIG 6
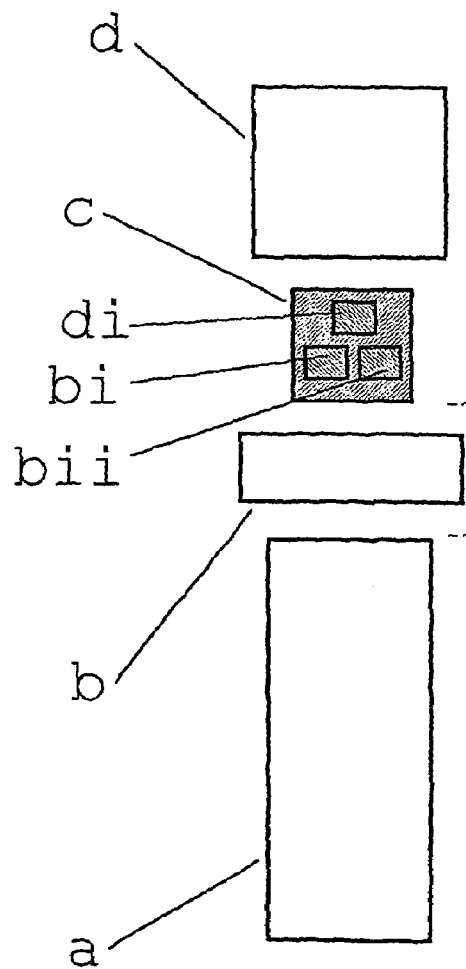
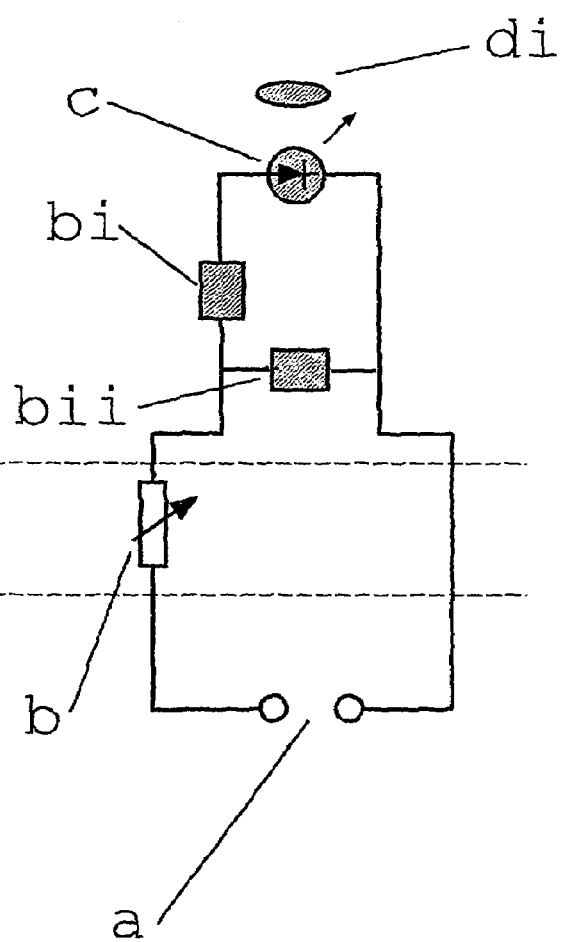

FIG 7
FIG 8
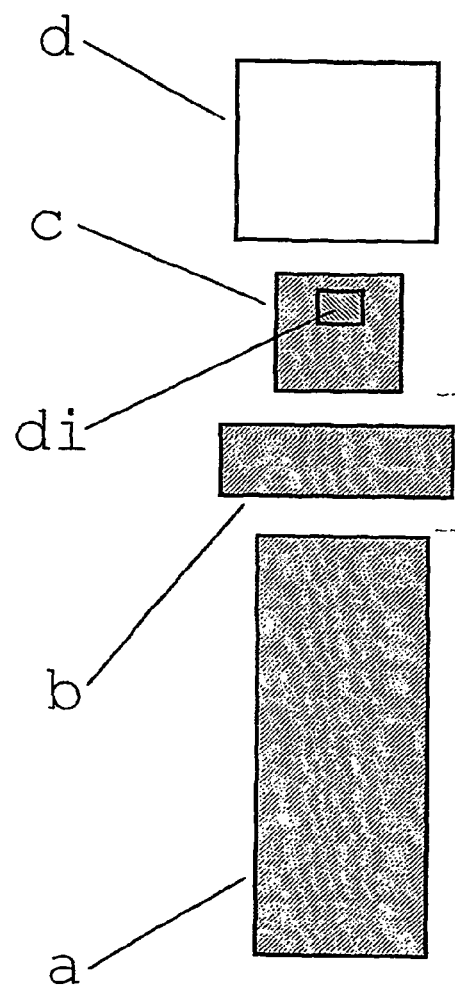
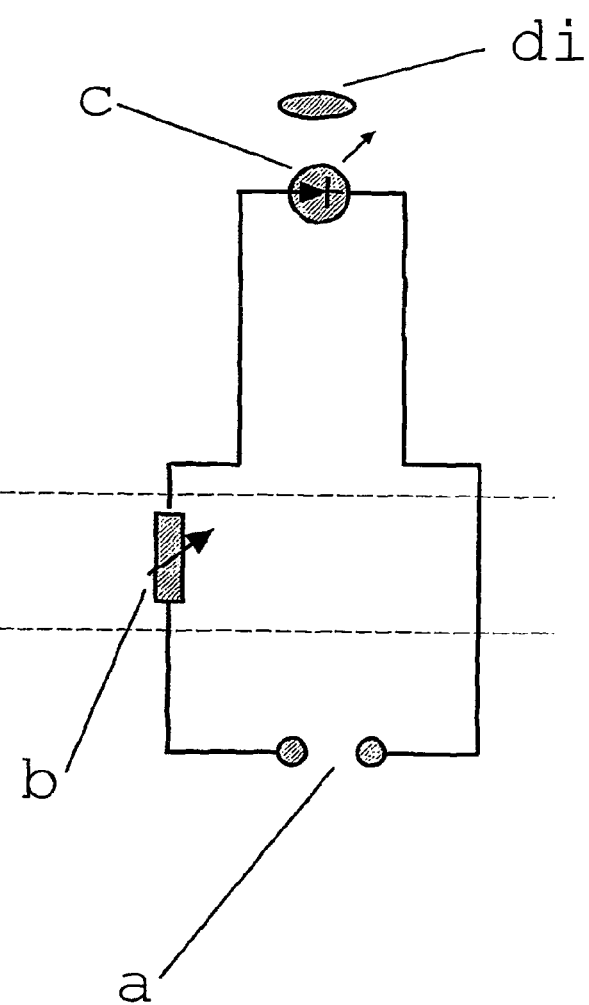

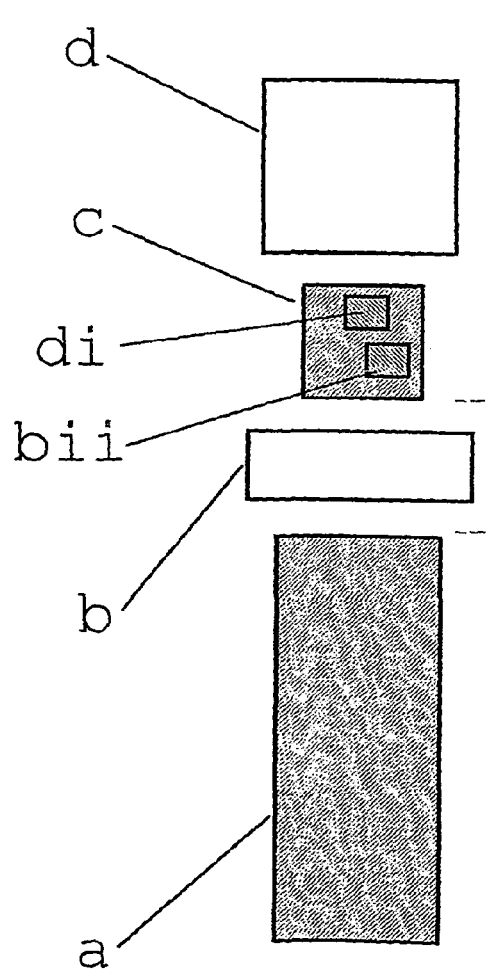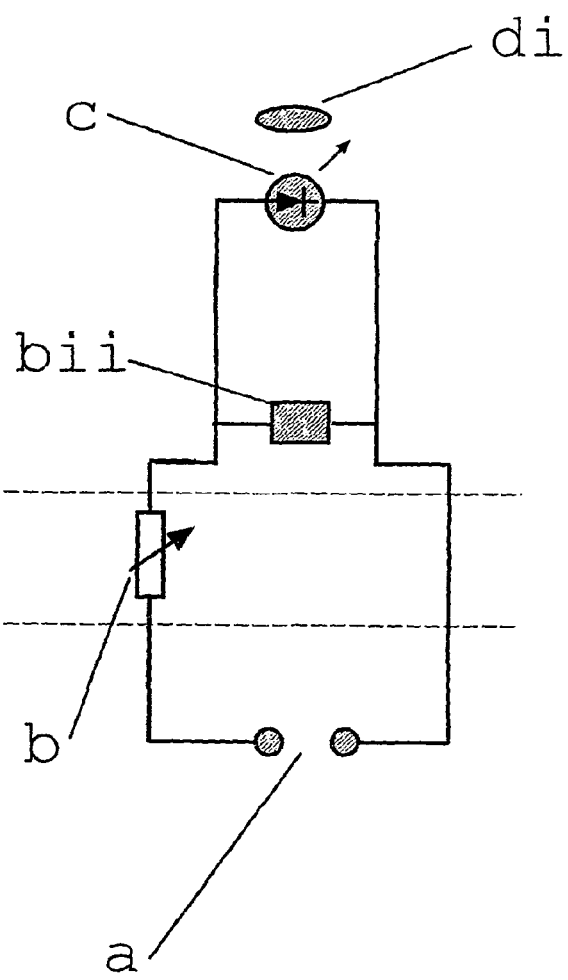

LIGHT SOURCE FOR DIAGNOSTIC INSTRUMENTS

TECHNICAL FIELD

The present invention relates to clinical diagnostic instruments which utilise a light source to illuminate the structure under scrutiny.

BACKGROUND

Instruments that are used for various diagnostic purposes such as the examination of eyes, ears, noses, and throats and other tissue structures often have a light source contained within the instrument enabling it to emit a light beam so as to illuminate the structure under observation. This is both convenient and practical. An image detection means (whether the human eye or otherwise) is used to register and interpret any resultant returning light.

Such an instrument may be functionally broken down into a number of smaller modules which each perform a discrete technical operation. Most instruments contain at least four modules in their construction, however extra modules may be added to enable additional functions to supplement those of the core modules.

The first module is an electrical power supply, which may be powered entirely by the mains with or without a transformer low voltage conversion, or a battery (either standard cells, rechargable cells or a combination of both). The latter battery type is preferred, especially the rechargable type especially when trickle charged because it enables the instrument to be portable and ready for use.

The second module is a means of controlling the electrical power which should be capable of handling the often high currents generated by the power supply whilst also being capable of varying the electrical power according to requirements. Conventional instruments utilise a heavy-duty ganged rheostat, which acts as an on/off switch and a current limiter thereby varying the electrical power which flows through the light source. The rheostat is typically of a low value (e.g. max resistance of ~8 ohm when first on, down to ~0 ohms in an approximately linear manner).

The third module is a means for generating light which typically is a light source element or elements. Conventional instruments typically use incandescent filament based bulbs that draw a large current (e.g. ~0.2 A to ~0.8 A) to enable an acceptable amount of visible light to be produced. Such bulbs are often of the halogen gas filled type which are usually of small size and are of a specialised nature.

The fourth module is a means for transforming the light, which may comprise lenses, filters, collimating means and other means to transform the light. This module is usually specialized for examining the structure under observation (e.g. eyes, ears etc).

An extra module that is commonly employed is a means of transforming any returning light from structure under scrutiny. This is often a rack of interchangeable lenses enabling fine focus of the light onto the image detection means.

The modules are typically combined together so as to produce a convenient, often handheld, combined instrument that is flexible and easy to use, whilst also enabling the instrument to be disassembled to enable replacement of modules (for example replacing expired bulbs). Although it is possible to change the fourth module to form a different instrument, in practice instruments are not usually used in this way and dedicated instruments are used for specific tasks.

To illustrate this, two widely used diagnostic instruments, namely an opthalmoscope (OS) and retinoscope (RS), will now be described. Both the OS and RS project a beam of light, which is used for examining the eye. Currently available handheld OS and RS have a dial (which is part of the rheostat control module) on the handle of the instrument, which enables light output to be smoothly and precisely varied. Such variability of the light beam is preferable for diagnostic purposes. An OS images a bright, small filament via lenses, mirrors and filters to produce a beam of light which is suitable for illumination of the eye. An RS images a bright, small, thin elongated filament in a similar way. The image detection means (usually the human eye) then receives any returned light, possibly via any fine focus lenses. In a typical clinical environment such an instrument may be in intermittent but repetitive use all day.

Although diagnostic instruments as described above based on filament bulb technology are widely used they suffer from numerous problems:

Filament bulbs have a limited life and eventually fail. In a typical clinical environment, depending on usage, this may occur as often as every six months. As a consequence such instruments are typically designed to allow the insertion of replaceable bulbs at periodic intervals by allowing separation of the instrument followed by reassembly.

Filament bulbs get hot during use due to dissipation of large amounts of infrared radiation which in turn is due to their inherent luminous inefficiency. Therefore such instruments are typically designed with a metal, or other heat conducting material, casing to act as a heat sink. A filament bulb will also usually have a container of similar construction, thus also acting as a heat sink.

Large amounts of infrared radiation is emitted in addition to useful visible light. As examination can often take a prolonged period of time this can often prove uncomfortable to the subject and/or have a possible deteriorating effect on the tissues under scrutiny. Thus, an infra red safety filter is typically incorporated within the fourth module to provide a 'cool' beam.

Due to the low luminous efficiency of filament bulbs they consume a high quantity of electrical power. Thus, for the instrument to be useful in a portable mode of operation, large batteries are needed. Additionally, a control apparatus capable of handling high power (e.g. a heavy rheostat) is needed.

The spectral light distribution of a filament bulb has a low colour-temperature (i.e. yellowy light). Some instruments incorporate a colour-correction filter to alter the light distribution. This is required to provide an improved colour-rendering-index factor, which is beneficial for analysis of biological tissues or other detailed tasks.

An incandescent filament emits its light flux effectively in all directions. This light usually has a high degree of coherence due to the small filament size. An optical condenser lens system is typically used to image this light source. To be efficient the condenser lens system should be close to the light source (to reduce light wastage) which necessitates it to be powerful in order to direct a portion of the light 'forwards'. This 'forwards' light is then usually projected by a field lens to a semi-silvered or sight-hole based, or other mirror. Much of the emitted light flux is thus not utilized and is absorbed within the instrument. There is usually no space in such instruments to have a reflector arrangement as an alternative to this.

Additionally, as bulbs for use in such instruments are required to have a small filament size (for efficient optical imaging purposes), they must be very accurately centered due to the requirements of the complex lens system.

The filament is surrounded by a fragile glass envelope. The operator must be very careful to avoid touching the glass, as grease from the fingers can cause cracks to develop on the glass envelope contributing to degradation and ultimately reducing the life of the bulb.

It is the aim of the present invention to overcome at least some of the above problems.

STATEMENT OF INVENTION

The present inventor has surprisingly found that clinical diagnostic instruments may be improved in a number of aspects if the light source is based on electroluminescent and/or phospholuminescent technology.

Thus the first aspect of the invention provides a clinical diagnostic instrument which comprises:
a means for supplying electrical power (a);
a means for controlling the electrical power (b);
a means for generating light (c);
a means for transforming the light prior to illumination of structure under scrutiny (d);

is characterised in that (c) is based on electroluminescent and/or phospholuminescent technology.

Another aspect of the invention provides for an instrument as defined above, characterised in that at least one of modules (a), (b) and (d) are designed for incandescent filament technology.

Another aspect of the invention provides for a use of the clinical diagnostic instrument for analysis of a structure under scrutiny.

Another aspect of the invention provides for a process of replacing the incandescent filament bulb of a clinical diagnostic instrument with (c), (b)(i) a module that allows an appropriate amount of electrical energy from (a) via (b) to be converted to light energy by (c), (b)(ii) a supplementary module that allows a discrete step and/or a variation (at any rate of change) between 0 and 100% of the available electrical power to be converted to light energy by (c), and (d)(i) a module that allows transformation of light prior to transformation by (d).

Another aspect of the invention provides for a process of replacing the incandescent filament bulb, the means for supplying electrical power and the means for controlling the electrical power of a clinical diagnostic instrument with (c), (a) and (b) both designed for (c), and (d)(i) a module that allows transformation of light prior to transformation by (d).

DETAILED DESCRIPTION OF THE INVENTION

LED Technology

The preferred embodiment light source is Light Emitting Diode technology (LEDs). Other non-incandescent filament bulb sources of light are conceivable such as light-emitting polymers or LASERs. Each will have different optoelectrical properties as will different generations of a single technology over time.

The advantages of LEDs as incorporated within a new design are numerous.

The lifetime of LEDs, when run at manufacturers recommended rating, can be as long as 100,000 hours. Even when run beyond their recommended rating, their lifetime can still be very long compared to analogous incandescent filament type bulbs. Since the lifetime of the LED is approximately the same as the useable life of the instrument as a whole, there would be no need to ever replace a bulb. As a result a new design of instrument may be constructed in one piece thus providing simpler manufacture.

Most commercially available LEDs give a light flux output that is directional from a narrow solid angle to wide (typically in a solid angle of from 8°-180°). Thus, wasteful light may be reduced or even eliminated entirely. Since LEDs emit light 'forwards' and also produce only low levels of infrared radiation, a reduced heat-sinking requirement of the casing is needed.

Since LEDs produce a 'cool' beam the need for a safety or infrared filter is negated. Thus this again allows for simpler manufacture.

LEDs also consume a much reduced quantity of electrical power which could enable smaller capacity batteries to be fitted. Alternatively, the batteries designed for incandescent filament bulbs may still be employed but enjoying a longer charge life. The heavy, large power rated rheostat could also be replaced with a lighter means of control.

Spectral light distribution of a white LED gives an almost ideal colour-rendering-index factor (ideally a colour temperature of around 6500K). As a result no colour correction filter is needed thus simplifying overall design.

Commercially available LEDs are supplied encapsulated in a plastic surround (micro-lensed). The shape of-the surround alters the light flux directionality. Alternatively, the same result may be achieved by external optical means or a combination of both approaches. The light source point area (unencapsulated ~0.75 mm$^2$) can thus be varied from an approximation to a point source with a high degree of coherence (<1 mm$^2$) through to an extended line source to a larger area (~5 mm$^2$). As a result, the light emitted from an encapsulated LED is much easier to directly adapt and change than that from filament bulb types.

Individual LEDs may be combined in an array configuration to form the module e.g. red, green or blue types or two white types etc.

The light source is protected by an encapsulating surround, which is impervious to most chemical attack and is impact resistant.

The improved light source allows for a number of preferred embodiments of the invention.

The New Instrument

In the first preferred embodiment of the invention, an entirely new design of all four modules is provided which incorporates the above advantages into a new instrument.

The means for supplying electrical power (a) may supply any quantity of power suitable for diagnostic instruments, typically this is at most 100 watts, preferably at most 20 watts, more preferably at most 5 watts, and most preferably at most 2 watts. The power may be provided from the mains or from a portable battery, but preferably it is from a battery to enable maximum flexibility in use. Such a battery, if present, will preferably have a capacity of no more than 50 Ahr, preferably no more than 20 Ahr, more preferably no more than 5 Ahr and most preferably no more than 2 Ahr. These batteries will typically be physically smaller than those required for incandescent filament bulb technology.

The means for controlling the electrical power (b) has the primary function of allowing a fraction of the available power to flow to the light source. Such a means may allow a discrete step and/or a variation (at any rate of change) between 0 and 100% of the available electrical power to be converted to light energy by (c). This function is preferably provided by a ganged rheostat or a ganged potentiometer circuit or a pulse code modulation circuit or some other electronic means.

If a rheostat is present its resistance value will be quite different to that used in conventional incandescent filament instruments, typically up to the resistance of the new light source (e.g. LED). The ideal resistance range variation would be one perfectly tailored to the optoelectrical characteristics of the new light source. An approximately linear design however is sufficient for most purposes. The voltage is controlled giving corresponding light output variance as a result. For example a typical white LED run at full light intensity requires a voltage of ~3.9V and ~2.9V for low light intensity. A voltage change of ~1.0V is thus produced as required.

The means for generating light (c) preferably provides a pre-transformed light with a luminous intensity of at most 2000 lumens, preferably at most 400 lumens, more preferably at most 100 lumens, most preferably at most 40 lumens. Such a light source is based on electroluminescent and/or phospholuminescent technology such as LEDs, light-emitting polymers or LASERs, although LEDs are preferred technology. The light emitted is preferably white light, preferably at a colour temperature of from 3500 to 15,000 Kelvin, more preferably from 4500 to 9000 Kelvin, most preferably from 6000 to 7000 Kelvin.

Since the new light source may direct the light 'forwards' the means for transforming the light prior to illumination of structure under scrutiny (d) may be of much simpler construction than that used for incandescent filament bulb technology. Preferably (d) has no more than six condenser or field lenses, more preferably no more than three, most preferably one. Preferably (d) is devoid of a colour-temperature correction and/or a heat absorbing filter.

Once the light has illuminated the structure under scrutiny, it may optionally be transformed prior to reception by the detection means (whether the human eye or otherwise). Hence the instrument may also comprise (e) a means for transforming the light returning from the structure under scrutiny. As with incandescent types this is often a rack of interchangeable lenses enabling fine focus on image detection means.

The modules comprising the instrument are typically contained within a suitable exterior casing to enable ease of use and to provide protection. Instruments based on incandescent filament technology usually need to have separable casings to enable expired bulbs to be replaced. The new instrument may conveniently be manufactured in one piece, using less metal or other such heat conducting material for heat sinking. Hence dense materials of construction are not essential to the overall design and preferably have an average bulk density of no more than 4000 kg/m$^3$, preferably no more than 2000 kg/m$^3$, more preferably no more than 1000 kg/m$^3$.

The Part-Adapted Instrument

Since the vast majority of clinical diagnostic instruments in use are based on incandescent filament technology, the present invention allows for replacement modules which are compatible with parts of diagnostic instruments based on incandescent filament technology. Accordingly the present invention provides for a series of clinical diagnostic instruments, that are characterised in that (c) is based on electroluminescent and/or phospholuminescent technology and at least one of modules (a), (b) and (d) are designed for incandescent filament technology. Accordingly these embodiments of the invention provide at least some of the above detailed advantages relating to the new light source. This would be a very cost effective way of deriving benefits of new light source.

Since electroluminescent and/or phospholuminescent light sources have very different electrical characteristics compared to conventional incandescent filament bulbs, they cannot simply be used as direct replacements and be expected to derive an acceptable light generation and thus optical performance in such instruments There are three main problems which must be overcome before they may be used as such.

The first problem is that the voltage produced by the power supply in conventional instruments is either much greater or much less than the new light source requires. Thus the new light source would draw too large a current and be damaged and possibly destroyed or draw too little current to be effective in the role intended. If (b) is designed for incandescent filament technology then a supplementary module must be added that can 'modify' control function of conventional (b).

If (b) is designed for incandescent filament technology, the problem of the power supply being too high may be overcome by providing a current limiter (b)(i) into the circuit. There are many ways of embodying this, each with their own advantages and disadvantages, one way to do this is via a low value resistor which causes a small but necessary voltage drop. If the power supply is too low (b)(i) may be a voltage boost circuit that draws its own power from the supply. Thus (b) (i) may be a switched mode circuit either using an inductor or of flying capacitor design, these designs can be used whether the power supply is too high or too low. Alternatively an oscillator/transformer type can be employed. Thus if (a) is designed for incandescent filament technology optoelectrical requirements, then the instrument also comprises a module (b)(i) that allows an appropriate amount of electrical energy from (a) via (b) to be converted to light energy by (c).

Alternatively this first problem may be overcome by providing a (b) which is specially designed for the new light source (e.g. rheostat value cut off point not dropping to zero ohms). Thus if (a) is designed for incandescent filament technology optoelectrical requirements, module (b) allows an appropriate amount of electrical energy from (a) via (b) to be converted to light energy by (c). Hence (b) would comprise a voltage reduction circuit (e.g. a resistor), or a voltage boost circuit such as a switched mode or oscillator/transformer and a device which allows a discrete step and/or a variation (at any rate of change) between 0 and 100% of the available electrical power to be converted to light energy by (c).

The second problem is that the means for controlling the electrical power in conventional instruments provides little or no variability of light output of (c) due to a lack of a significant voltage drop across (c) through range of resistance. This is caused by the low resistance (yet high power rating) value of the control rheostat which is designed specifically to cater for the optoelectrical characteristics of incandescent filament light sources (namely low hot resistance/high current). There are many ways of solving this problem, each with their own advantages and disadvantages, for example via a resistor connected in parallel across the voltage supply. Other ways include a negative resistance circuit or an amplifier which is variable in proportion to a sense current which is in turn proportional to the current flowing through a load. Another solution may use pulse code modulation or other electronic control means. Thus if the means for controlling the electrical power (b) is designed for incandescent filament bulb technology (e.g. a low value rheostat) it must also comprise an I/V converter module (b)(ii), that allows a discrete step and/or a variation (at any rate of change) between 0 and 100% of the available electrical power to be converted to light energy by (c). If present (b)(ii) is a resistor or a sense current/amplifier based circuit or other electrical circuit means.

The third problem is that it is also conceivable that the replacement light source module may need to be used with a means for transforming the light (d) designed for incandescent filament bulb technology. If so, then module (d)(i) is essential which allows transformation of light prior to further transformation by (d). If present (d)(i) comprises a lens, a micro-lens, a holographic optical element or diffraction grating. In a preferred embodiment (c) is based on LED technology and (d)(i) is rigidly attached to (c). If present (d)(i) may comprise a lens with a dioptric modulus power of at least 100 D, preferably at least 1000 D, more preferably at least 3000 D. Additionally (d)(i) may comprise a lens with a dioptric power of (d)(i) is at most 100 D, preferably at most 30 D, more preferably at most 10 D, most preferably substantially zero D.

In a second preferred embodiment (EMB 2) the present invention provides for a clinical diagnostic instrument wherein (c) is based on electroluminescent and/or phospholuminescent technology, and (a), (b) and (d) are designed for incandescent filament technology and (b)(i), (b)(ii) and (d)(i) are present. It is preferred that (c) and at least one of (b)(i), (b)(ii) and (d)(i) are surrounded by a single casing so that (c) may be fitted to an existing instrument designed for incandescent filament technology. Accordingly this embodiment provides for a new replacement bulb.

In a third preferred embodiment (EMB 3) the present invention provides for a clinical diagnostic instrument wherein (c) is based on electroluminescent and/or phospholuminescent technology for which both (a) and (b) are specifically designed but (d) is designed for incandescent filament technology. Accordingly (d)(i) is present, but both (b)(i) and (b)(ii) are not present. It is preferred that (c), (a), (b) and (d)(i) are surrounded by a single casing so that the resultant device may be fitted to an existing module (d) designed for incandescent filament technology. Accordingly this embodiment provides for a new combined light source/controller/power supply device that attaches to a conventional (d).

In a fourth preferred embodiment (EMB 4) the present invention provides for a clinical diagnostic instrument wherein (c) is based on electroluminescent and/or phospholuminescent technology for which (a) is specifically designed but both (b) and (d) are designed for incandescent filament technology. Accordingly (b)(ii) and (d)(i) are present but (b)(i) is not present. Accordingly this embodiment provides for a new light source/power supply device to be fitted between conventional (b) and (d).

In a fifth preferred embodiment (EMB 5) the present invention provides for a clinical diagnostic instrument wherein (c) is based on electroluminescent and/or phospholuminescent technology for which (b) is specifically designed but both (a) and (d) are designed for incandescent filament technology. Accordingly (d)(i) is present but neither (b)(i) nor (b)(ii) are present. Accordingly this embodiment provides for a new light source/controller device fitted to conventional (a) and (d)

There are many other embodiments that utilise some conventional and new modules.

The invention will be now illustrated, but in no way limited by, the following examples.

(Note: for following Figs shaded regions indicate new parts.)

Figure 12:
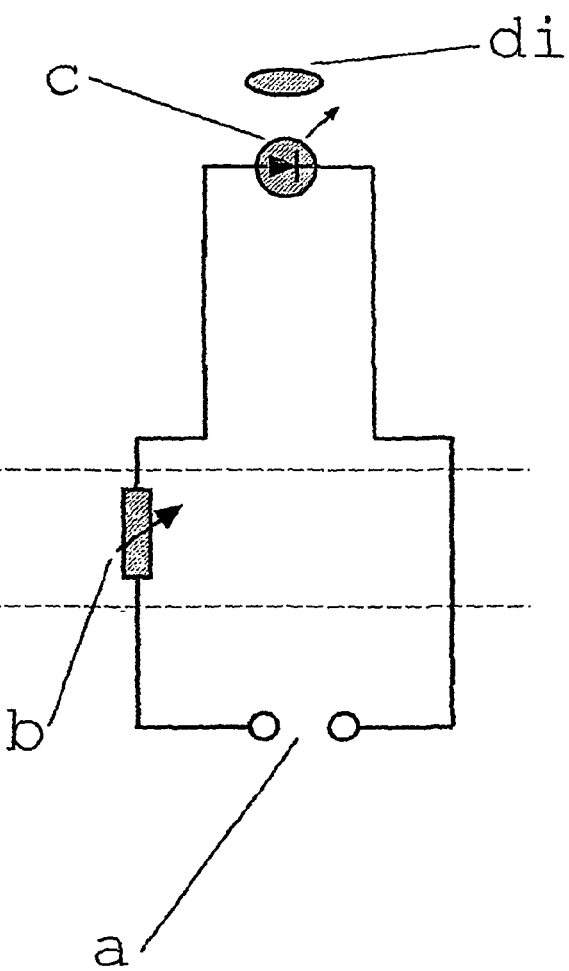
Figure 13:
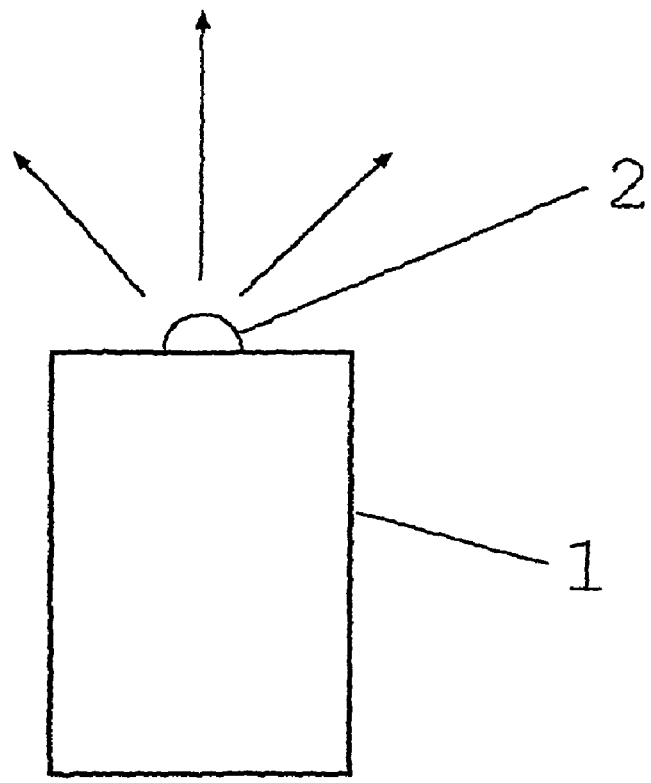
Figure 14:
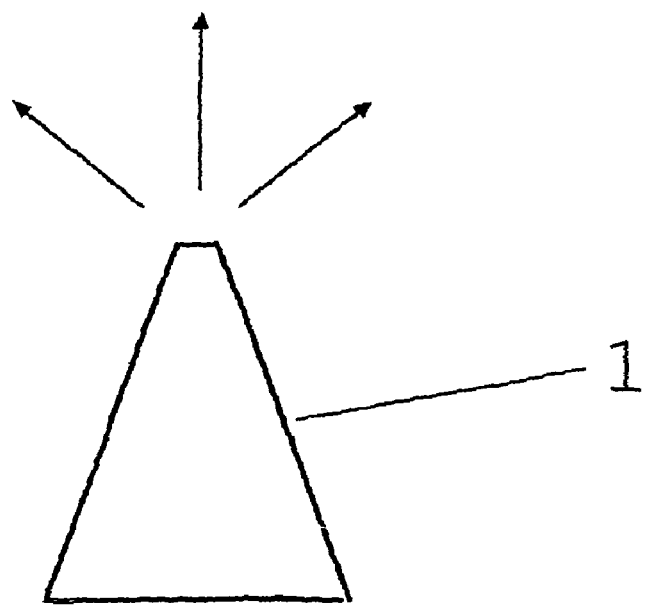
Figure 15:
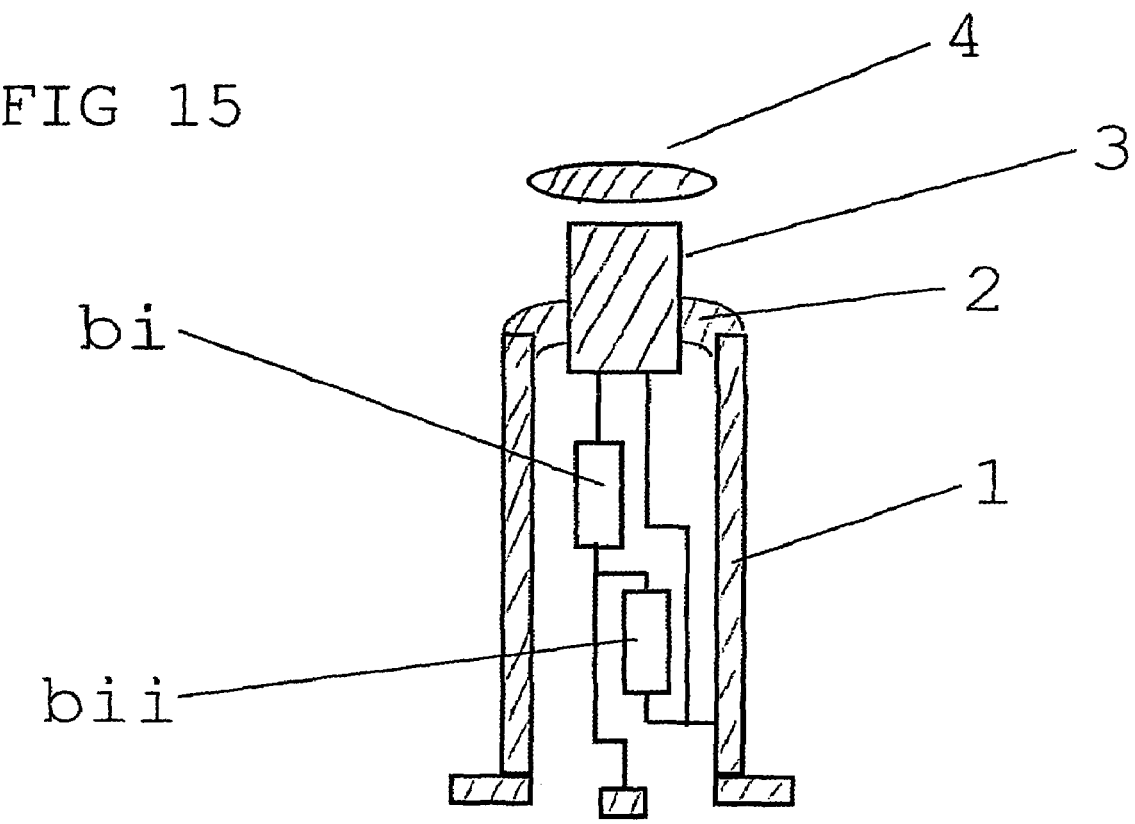
Figure 16:
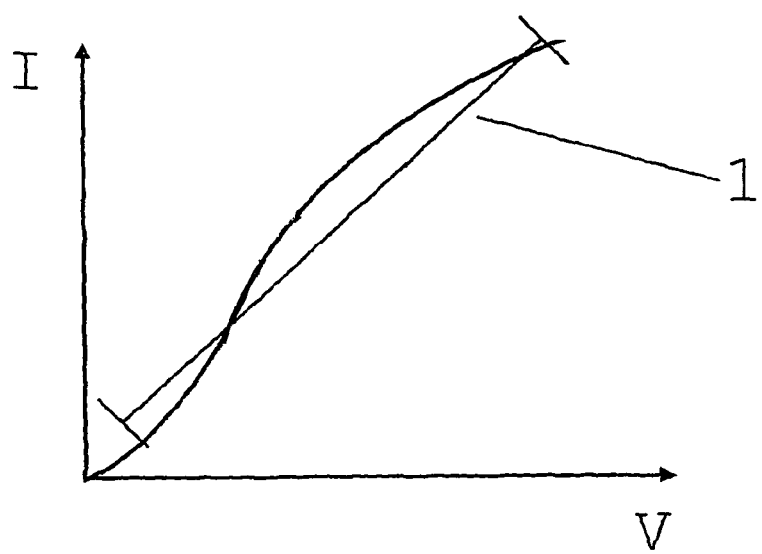
Figure 17:
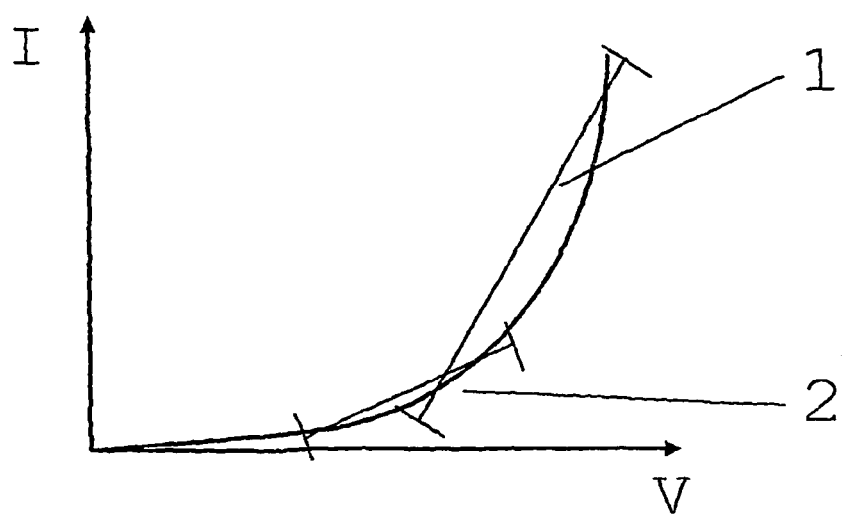

FIG. 1 Prior art block diagram.
FIG. 2 Circuit diagram of prior art.
FIG. 3 Block diagram of the new instrument EMB 1.
FIG. 4 Circuit diagram of the new instrument EMB 1.
FIG. 5 Block diagram of EMB 2.
FIG. 6 Circuit diagram of EMB 2.
FIG. 7 Block diagram of EMB 3.
FIG. 8 Circuit diagram of EMB 3.
FIG. 9 Block diagram of EMB 4.
FIG. 10 Circuit diagram of EMB 4.
FIG. 11 Block diagram of EMB 5.
FIG. 12 Circuit diagram of EMB 5.
FIG. 13 Side view of an encapsulated LED (with microlens).
FIG. 14 Side view of an encapsulated LED (as a slit).
FIG. 15 Side view of physical embodiment of EMB 2.
FIG. 16 Graph of I/V of an incandescent bulb.
FIG. 17 Graph of I/V of an LED.

FIG. 1 shows prior art block diagram of instrument, showing the modules. The prior art FIG. 1 shows the electrical power supply (a), the control module (b), the light source (c), and the transformation module (d) as separate units in their usual arrangements. These units are combined together so as to produce the final instrument. FIG. 2 shows circuit diagram of prior art instrument. FIG. 2, shown alongside FIG. 11, shows the internal circuitry required to operate the instrument.

FIG. 3 shows block diagram of the new instrument, showing combined modules. FIG. 3 shows the preferred embodiment of the first aspect of the invention, the new instrument, showing how the transformation, light source, power and control modules are combined to provide new instrument with new casing design. FIG. 4 shows circuit diagram of the new instrument. FIG. 4, shown alongside FIG. 3, shows how the internal circuitry is similar in layout to that of a conventional filament bulb instrument (see FIG. 2) but differs in the light source, control and power functions.

FIG. 5 shows block diagram of preferred embodiment two. FIG. 5 shows the new light source module, incorporating the (b)(i), (b)(ii) and (d)(i). FIG. 6 shows circuit diagram of new preferred embodiment two. FIG. 6, shown alongside FIG. 5 shows how (b)(i) and (b)(ii) are arranged schematically. (d)(i) is also shown in relative position.

FIG. 7 shows block diagram of preferred embodiment three. This variation retains original (d) but has new (a), (b) and (c) together with (d)(i). FIG. 8 shows circuit diagram of preferred embodiment three shown alongside FIG. 7 together with relative position of (d)(i).

FIG. 9 shows block diagram of preferred embodiment four. This variation retains original (d) and (b) but has new (a) and (c) together with (b)(ii) and (d)(i). FIG. 10 shows circuit diagram of preferred embodiment four shown alongside FIG. 9 which shows how (b)(ii) is arranged schematically. (d)(i) is also shown in relative position.

FIG. 11 shows block diagram of preferred embodiment five. This variation retains original (d) and (a) but has new (b) and (c) and (d)(i). FIG. 12 shows circuit diagram of preferred embodiment five shown alongside FIG. 11 which shows how (d)(i) is also shown in relative position.

FIG. 13 shows side view of an LED with encapsulation (1) with a substantially zero dioptric power (i.e. flat top) which has a micro-lens (2) mounted over light emitting area (not shown) thus enabling forward imaging of light whilst from a physically small area. FIG. 14 shows side view of an LED with encapsulation (1) formed so that a long thin source of light results. FIG. 15 shows side view of physical embodiment of second preferred embodiment (new replacement bulb), incorporating means to alter function of other modules. (b)(i) (either current limiter or voltage boost configuration) is shown. An I/V converter (as second problem) is shown as (b)(ii). A connector/case is shown in (1), these are used to connect the light source module to the power supply. This is typically made of an electrically conductive material. The case has the multiple functions of holding the contents secure, acting as a heat sink and also possibly as a connector to the power supply. A holder (2) performs the function of supporting the light source; it may also act as a heat sink. The light source itself (3) is housed so that the light is directed in one direction. Any additional optics or method of altering encapsulating optics of (LED) itself may be needed to alter the light as so required; here a lens is shown (4).

FIG. 16 shows graph of typical filament bulb I/V electrical characteristics. Line (1) shows change, typically described as an 'S' shape. FIG. 17 shows graph of I/V electrical characteristics of typical LED. The line (1) extends from a high current value to a low value: i.e. big difference. The line is roughly in line with actual I/V change needed to produce acceptable light output variance. In contrast line (2) is only analogous over a very small range: i.e. poor light variance.

The invention claimed is:

1. An clinical diagnostic instrument which is an ophthalmoscope or retinoscope which comprises:
    a means for supplying electrical power (a);
    a means for controlling the electrical power (b);
    a means for generating light (c);
    a means for transforming the light prior to illumination of structure under scrutiny (d) including at least one condenser lens;
    a means for transforming the light returning from the structure under scrutiny (e);
    wherein (c) is based on electroluminescent and/or phospholuminescent technology and emits white light, at a color temperature of from 3500 to 15,000 Kelvin.

2. A diagnostic instrument according to claim 1, wherein (a) provides a power output of at most 100 watts.

3. A diagnostic instrument according to claim 1 or claim 2, wherein (a) is a battery.

4. A diagnostic instrument according to claim 3, wherein the battery has a capacity of no more than 50 Ahr.

5. A diagnostic instrument according to claim 1, wherein (b) allows a discrete step and/or a variation (at any rate of change) between 0 and 100% of the available electrical power to be converted to light energy by (c).

6. A diagnostic instrument according to claim 5, wherein (b) comprises a ganged rheostat or a ganged potentiometer circuit or a pulse code modulation circuit.

7. A diagnostic instrument according to claim 1, wherein (c) provides a pre-transformed light luminous intensity of at most 2000 lumens.

8. A diagnostic instrument according to claim 1, wherein (c) is based on LED technology.

9. A diagnostic instrument according to claim 1, wherein (d) has no more than six condenser and field lenses.

10. A diagnostic instrument according to claim 1, wherein the instrument is surrounded by at least one casing.

11. A diagnostic instrument according to claim 10, wherein the instrument is surrounded by a single casing.

12. A diagnostic instrument according to claim 10 or claim 11, wherein the average bulk density of the casing is no more than 4000 kg/m$^3$.

13. A diagnostic instrument according to claim 1, wherein at least one of modules (a), (b) and (d) are designed for incandescent filament technology.

14. A diagnostic instrument according to claim 13, wherein (a) is designed for incandescent filament technology optoelectrical requirements, and comprises a module (b)(i) that allows an appropriate amount of electrical energy from (a) via (b) to be converted to light energy by (c).

15. A diagnostic instrument according to claim 14, wherein (b)(i) is a voltage reduction circuit comprising a resistor, or a voltage boost circuit such as a switched mode or oscillator/transformer.

16. A diagnostic instrument according to claim 13, wherein (a) is designed for incandescent filament technology optoelectrical requirements, and module (b) allows an appropriate amount of electrical energy from (a) via (b) to be converted to light energy by (c).

17. A diagnostic instrument according to claim 16, wherein (b) comprises a voltage reduction circuit (e.g. a resistor), or a voltage boost circuit such as a switched mode or oscillator/transformer and a device which allows a discrete step and/or a variation (at any rate of change) between 0 and 100% of the available electrical power to be converted to light energy by (c).

18. A diagnostic instrument according to claim 13, wherein (b) is designed for incandescent filament technology optoelectrical characteristics, and comprises a module (b)(ii), that allows a discrete step and/or a variation (at any rate of change) between 0 and 100% of the available electrical power to be converted to light energy by (c).

19. A diagnostic instrument according to claim 18, wherein (b) comprises a low value rheostat.

20. A diagnostic instrument according to claim 18 or claim 19, where (b)(ii) comprises a resistor or a sense current/amplifier based circuit or other electrical circuit means.

21. A diagnostic instrument according to claim 13, wherein (d) is designed for incandescent filament technology for size and/or shape of light emitting region and/or light flux distribution, and also comprises a module (d)(i) that allows transformation of light prior to transformation by (d).

22. A diagnostic instrument according to claim 21, where (d)(i) comprises a lens, a micro-lens, a holographic optical element or diffraction grating.

23. A diagnostic instrument according to claim 21 or claim 22, where (c) is based on LED technology and (d)(i) is rigidly attached to (c).

24. A diagnostic instrument according to claim 21, wherein the modulus of the dioptric power of (d)(i) is at least 100 D.

25. A diagnostic instrument according to claim 19, wherein the modulus of the dioptric power of (d)(i) is at most 100 D.

26. A diagnostic instrument according to claim 21, wherein (a), (b) and (d) are designed for incandescent filament technology and (b)(i), (b) (ii) and (d) (i) are present.

27. A diagnostic instrument according to claim 21, wherein (a) and (b) are designed for (c), (d) (i) is present and neither (b)(i) nor (b)(ii) are present.

28. A diagnostic instrument according to claim 21, wherein (b) and (d) are designed for incandescent filament technology, (a) is designed for (c), both (d) (i) and (b) (ii) are present and (b) (i) is not present.

29. A diagnostic instrument according to claim 21, wherein (a) and (d) are designed for incandescent filament technology, (b) is designed for (c), (d)(i) is present and both (b)(i) and (b)(ii) are not present.

30. A diagnostic instrument according to claim 13, wherein (c) and at least one of (b)(i), (b)(ii) and (d)(i) are surrounded by a single casing.

31. A diagnostic instrument according to claim 26, wherein (c), (b)(i), (b)(ii) and (d)(i) are surrounded by a single casing.

32. A diagnostic instrument according to claim 27, wherein (c), (a), (b) and (d)(i) are surrounded by a single casing.

* * * * *